United States Patent [19]

Firth

[11] Patent Number: 5,232,856
[45] Date of Patent: Aug. 3, 1993

[54] ELECTROPORATION DEVICE

[76] Inventor: Kevin L. Firth, 487 Victoria Street, Kingston, Ontario, Canada, K7L 3Z8

[21] Appl. No.: 559,669

[22] Filed: Jul. 30, 1990

[51] Int. Cl.$^5$ .................... C12N 13/00; C12M 1/00
[52] U.S. Cl. .................... 435/287; 435/172.1; 435/173.6; 435/817; 935/52; 935/85; 204/403; 204/299 R
[58] Field of Search .................. 435/287, 172.1, 172.2, 435/172.3, 173, 817; 935/52, 85; 204/180.1, 180.3, 299 R, 403

[56] References Cited

U.S. PATENT DOCUMENTS

| | | | |
|---|---|---|---|
| 4,441,972 | 4/1984 | Pohl | 204/299 R |
| 4,476,004 | 10/1984 | Pohl | 204/299 R |
| 4,622,302 | 11/1986 | Sowers | 435/172.2 |
| 4,661,451 | 4/1987 | Hansen | 435/288 |
| 4,663,292 | 5/1987 | Wong et al. | 435/287 |
| 4,695,547 | 9/1987 | Hilliard et al. | 435/289 |
| 4,699,881 | 10/1987 | Matschke | 435/287 |
| 4,784,954 | 11/1988 | Zimmermann | 435/173 |
| 4,800,163 | 1/1989 | Hibi et al. | 435/287 |
| 4,804,450 | 2/1989 | Mochizuki et al. | 435/287 |
| 4,822,470 | 4/1989 | Chang | 435/172.1 |
| 4,832,814 | 4/1989 | Root | 435/172.2 |
| 4,849,089 | 7/1989 | Marshall, III | 435/287 |
| 4,849,355 | 7/1989 | Wong | 435/172.3 |
| 4,882,281 | 11/1989 | Hilliard et al. | 435/287 |
| 4,906,576 | 3/1990 | Marshall, III | 435/287 |
| 4,910,140 | 3/1990 | Dower | 935/52 |
| 4,923,814 | 5/1990 | Marshall, III | 435/173 |
| 4,946,793 | 8/1990 | Marshall, III | 435/291 |
| 5,007,995 | 4/1991 | Takahashi et al. | 435/273 |
| 5,019,034 | 5/1991 | Weaver et al. | 604/20 |
| 5,098,843 | 3/1992 | Calvin | 435/287 |

FOREIGN PATENT DOCUMENTS 1208146 7/1986 Canada .

OTHER PUBLICATIONS

Yaoita et al., "Potential-Controlled Morphological Change and Lysis of HeLa Cells Cultured on an Electrode Surface", Biochemistry and Bioenergetics, 20:169–177, 1988.

Primary Examiner—Robert J. Warden
Assistant Examiner—T. A. Trembley

[57] ABSTRACT

An electroporation apparatus provides for the electroporation of cells attached to an electrode. The electrode may be transparent to allow cell viewing. If the electrode exhibits a voltage drop a constant electrical field may be obtained over the cell layer by controlling the position or character of the opposed electrode. Alternately, cells may be electroporated under an electrical field which varies in a continuous, geometrically uniform manner over the cell layer.

24 Claims, 9 Drawing Sheets

- ● % CELLS FLUORESCING
- ▲ % CELL DEATH
- ■ HYGROMYCIN RESISTANT COLONIES

ELECTROPORATION DEVICE

FIELD OF THE INVENTION

This invention relates to an improved device and method for introducing biological macromolecules like proteins, nucleic acids (DNA or RNA) or other nonpermeant molecules like dyes, various nucleotides or drugs into living cells by means of an electric field or current. This procedure is known as "electroporation".

BACKGROUND OF THE INVENTION

Electroporation is a recently identified procedure by which nonpermeant molecules may be introduced into the cell through the cell wall using an electric field. A prior art patent purporting to achieve this effect with respect to DNA is that of T. Wong, U.S. Pat. No. 4,849,355. In this, as in other electroporation procedures discussed in the literature, the cells to be electroporated were held in suspension in an electrolytic solution.

Experience to date has shown that while the rate of cell penetration can be improved by selecting the applied electrical voltage, as the voltage increases, a point is reached where cell mortality increases substantially. Apparently, successful electroporation, in terms of elevated the percentage of cells into which the desired molecules are introduced, combined with minimal cell damage, occurs only over a narrow range of applied voltages. More precisely, it is assumed that it is the electrical field strength, in volts per centimeter in the vicinity of the subject cells that is a major parameter in achieving successful electroporation, or the electrical current that corresponds to such electrical field.

In one article, "Electroporation and DNA Transfer" by Joyce L. Knutson and Daniel Yee, Analytical Biochemistry 164, 44–52 (1987), reference is made to the intensity of the electrical field as a parameter governing successful electroporation. Pulsed electric fields having momentary strengths on the order of 3.5 kV/cm and 8 kV/cm are recited as having been used by earlier researchers. In this specific article field strengths of around 390–1060 V/cm were applied.

The electroporation chamber described by Knutson and Yee consisted of 1 cm wide aluminum foil electrodes, 1 cm apart. Presumably the field in this set-up was calculated by dividing the applied voltage, during discharge, by the separation distance of the electrodes, and by assuming that the phosphate-buffered saline solution forming the electrolyte in the electroporation chamber was amorphous.

Further this article hypothesizes that with a constant field existing across an electroporation chamber, the voltage drop across each cell in suspension is concentrated across the relatively non-conductive cell membrane. Thus this article supposes that break-down of the cell membrane of the mammalian-type cells being tested occurs when the voltage drop across the cell membrane is around 200 mV. It is thereby supposed that "pores" effective for electroporation occur under similar voltage conditions.

Accordingly, as is apparent from this and other articles in the literature, control over the strength of the electric field to which cells are exposed, or the electrical current equivalent, is considered to be an important parameter for successful electroporation.

All of the work on electroporation so far cited in the literature except Chang deals with cells in suspension, that is either cells normally growing as a suspension, such as cells of hemopoietic origin, or cells which normally grow while attached to a solid support (cells of fibroblast or epithelial origin) but which have been detached for the occasion through the use of proteolytic enzymes or EDTA (Ethylenediamine tetraacetate) to place them in suspension This detachment, however, disturbs cellular metabolism in general and especially the cell division cycle. This latter effect is shown by a substantial delay in cell entry into the S (DNA synthesis) phase in the case of cells which have been detached. Therefore, a preferred procedure for electroporation of adherent cells is to apply the electric field while the cells are attached to their solid growth surface.

This arrangement has the advantage over conventional procedures in that naturally adherent cells need not be treated with a proteolytic enzyme, such as trypsin, in order to lift them into suspension for electroporation treatment. This avoids the disruption of cell physiology, especially with regard to their division cycle, inherent in their detachment, and allows studies of the effects of introduced-molecules to proceed without the complications associated with such disruption.

One method of electroporating cells while they adhere to a surface is to grow such cells on one of the electrodes of the electroporation chamber. For convenience of observing such cells under a microscope a transparent substrate with a transparent electrically conductive surface may be employed as such an electrode. A disadvantage of using an electrode of this form is that, due to electrical resistance, a voltage drop may develop over the area of the conductive surface, particularly where a thin conductive film is laid over a nonconducting glass or plastic substrate. This voltage drop will cause progressive regions of the cell population on the surface of the electrode to be exposed to electrical fields of differing intensity. This may result in only a portion of the cell population being exposed to fields of preferred intensity.

The foregoing problem is premised on the use of a conductive surface that exhibits significant resistive loss when employed as an electrode in an electroporation chamber. A converse problem arises when an electrode of low resistivity is employed for such surface, and it is desired to expose a surface population of adherent cells to an electric field which varies in a controlled manner over the area of such surface.

While recognition has been given to the significance of the strength of the applied field as a factor affecting successful electroporation, no attempts have been made to create a generally uniform electrical field over a surface carrying a population of living adherent cells that are proposed to be electroporated. Further no one has arranged to expose a surface population of cells to an electroporating field which varies, along the surface in a continuous, geometrically regular fashion.

It is, therefore, an object of this invention to create uniform field strength conditions over a surface carrying adherent cells so that a larger number of cells may be treated simultaneously to essentially the same field strength, and thereby more closely control the successful electroporation of living cells.

A further object of this invention is to provide an electrical field of continuous and of systematically varying strength, in a geometric sense, for electroporating a population of adherent cells on a surface, and thereby permit a direct comparison of the response of such cells to being electroporated under local electric fields of differing strengths.

These, and further features of the invention will be more apparent from the descriptions which no follow.

SUMMARY OF THE INVENTION

In accordance with the invention living cells attached to a partially conductive surface exhibiting a voltage drop upon passage of current therethrough are electroporated by exposing them simultaneously to an electrical field of substantially the same local electric field strength over the said surface.

More particularly in the case where the cells to be electroporated are distributed over a surface which serves as an electrode in an electroporation device and such electrode is only partially conductive and exhibits a voltage drop when current is passed therethrough, then, by applying the invention, such cells are then exposed to an electroporating electrical field which nevertheless has a substantially equal local field strength over a substantial portion of the electrode surface.

In another application of the invention, cells to be electroporated are exposed to an electrical field of varying strength over different regions on such surface.

A condition of substantially equal local electric field strength over a cell-bearing surface can be created by providing an electroporation apparatus comprising:

(a) first and second electrodes, each having an exposed surface, said electrodes being positioned to create an electric field there-between when connected to a source of electrical potential, said first electrode being only partially conductive and exhibiting a voltage drop upon the passage of current therethrough;

(b) an electrolyte positioned between said electrodes, said electrolyte containing molecules to be introduced into cells by the electroporation process and being in contact with said exposed surface of each of said electrodes;

(c) living cells in contact with said electrolyte, that are subject to said electrical field as part of the process of electroporation;

and by providing the improvement whereby:

(d) said cells are attached to the exposed surface of at least the first electrode, and (e) said second electrode, in combination with said first electrode provides a local electrical field at the surface of the first electrode which is of substantially equal strength over the exposed surface of said first electrode;

Alternately, a local electrical field may be created which is of a strength which changes in a continuous, geometrically regular manner along the surface of said electrode. In the case where a local electrical field of geometrically regular field strength e.g., a field that varies with a consistently increasing strength when proceeding in a given direction across the electrode surface, is provided, the first electrode may be substantially fully conductive and thereby display no voltage drop.

In accordance with one variant of the invention the first electrode is subject to a voltage drop which occurs along its surface during the procedure of electroporation, and the second electrode is spaced with respect to said first electrode so as to create said local electrical field of substantially equal strength over the exposed surface of said first electrode.

According to another embodiment of the invention the first and second electrodes are planar and the second electrode is angled with respect to said first electrode to create the local electrical field of substantially equal strength.

According to another embodiment of the invention the first and second electrodes are planar and the second electrode is angled with respect to the first electrode to create the local electrical field of a strength which varies in a continuous and geometrically regular manner over the surface of said first electrode.

By a further variation of the invention the first and second electrodes are planar, the second electrode is angled with respect to said first electrode to create the above referenced local electrical field and said local electric field varies linearly, progressing in one direction over the surface of said first electrode.

The features of the invention are also embodied in a further variation of the invention wherein the electrodes are planar, said first electrode is subject to a voltage drop which occurs along its surface during the procedure of electroporation, and said second electrode exhibits a voltage pattern along its exposed surface complementary to that occurring on the surface of said first electrode during the procedure of electroporation so as to create said local electrical field of substantially equal strength over the exposed surface of said first electrode.

By a further feature of the invention the first electrode comprises a thin, partially conductive planar film of constant thickness deposited on a substrate and a closed encircling elevated boundary wall formed around said planar film and positioned so as to serve as a containment means for said electrolyte.

By a further feature of the invention the substrate and film are sufficiently transparent or translucent to allow viewing of the cells on said exposed surface under a microscope.

These and further features of the invention will be better understood from the description of the preferred embodiments in relation to the figures which now follow.

SUMMARY OF THE FIGURES

FIG. 2 a is an exploded perspective view of a glass slide with a boundary wall that serves as containment means for use in the electroporation apparatus of FIG. 2;

DESCRIPTION OF THE PREFERRED EMBODIMENTS

Figure 1:
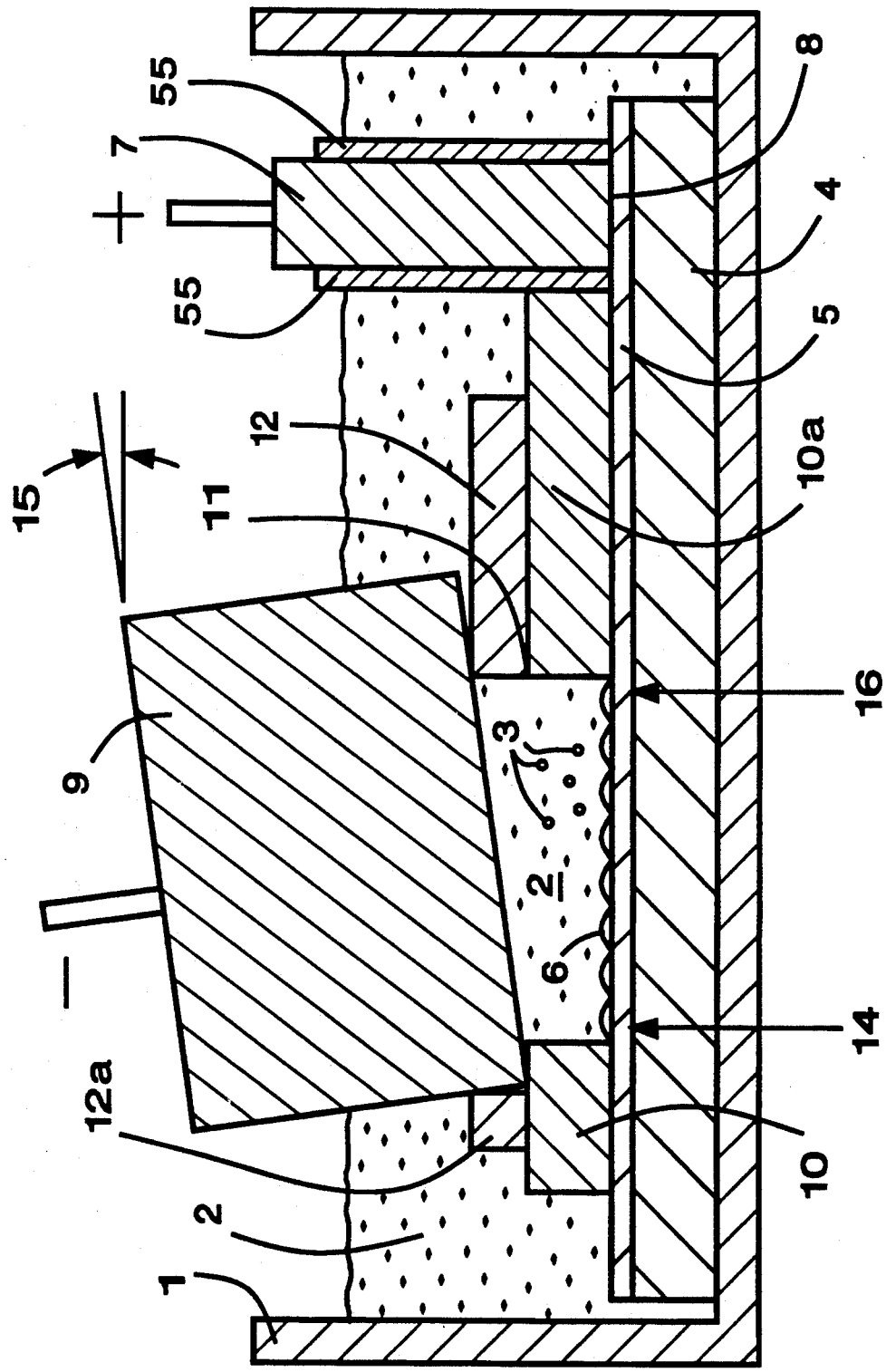
FIG. 1 shows an electroporation apparatus, within a petri dish, incorporating an inclined electrode arrangement.

In FIG. 1, the layout of components in an electroporation apparatus demonstrating the invention are shown. The outer chamber 1 maybe a glass or plastic petri dish, filled with an electrolyte medium 2, suitable for carrying molecules 3 to be electroporated.

A substrate 4, preferably in the form of a glass or plastic plate, is coated with a conductive surface layer 5 on which cells will grow. This plate may be the base of a petri dish, or may be a slide that can be inserted in a petri dish during cell cultivation.

A suitable surface layer 5 has been found to be tin oxide doped with indium, vacuum-deposited on glass (Donnelly Corp., Holland, Mich.).

The tin oxide coating was chosen because it is conductive and transparent at a low thickness, permitting the direct visualization of the treated cells. Moreover, it is inert, nontoxic to the cells, promotes excellent cell adhesion and is very durable. Indium-tin oxide coated glass slides can be sterilized and used repeatedly, even at high voltages, without any observable effect upon their conductivity, ability to permit efficient electroporation, or toxicity to the cells. An added advantage to this combination is the fact that, contrary to plastic petri dishes, this coating on glass does not exhibit any spontaneous fluorescence. This makes the examination of the electroporated cells in a fluorescent microscope possible. In this form, in slide format, cells may be readily viewed under a microscope in their attached condition.

A layer of cells 6 to be electroporated is caused to grow on the surface layer 5 prior to treatment. In the electroporation chamber 1 the surface layer is contacted at one end by a contact bar 7. A rectangular block of aluminum has been found satisfactory, its rectangular shape being used to provide current to the surface layer 5 along a line-boundary 8. To improve the electrical contact between the bar 7 and surface layer 5, a ridge may be formed along the boundary 8.

By reason of the choice of a thin film, imposed by the need for transparency, the surface layer 5 will exhibit a voltage drop over its surface, proceeding away from the contact bar boundary 8. It is believed that such voltage drop is substantially linear with distance from the bar, even during electroporation, when current passes through the surface layer 5 into the electrolyte 2.

The surface layer 5 performs as one electrode for the electroporation process. A second electrode 9 is mounted over the surface layer 5 supported by a first insulative spacer 10 at one end and a second insulative spacer 11 at the other end. Conveniently, the first spacer 10 can be of a monolithic form that surrounds the region to be electroporated and a shim 12 can be inserted to combine with the lower portion 10a of the surrounding spacer 10 to provide the second spacer 11. A stopping bar 12a also helps to position the upper electrode 9. To prevent the electrolyte 2 from providing a short circuit path between the elctrodes, an insulative barrier 55 may be provided.

In order to minimize the volume of electrolyte 2 and molecular bodies 3 required for the process, it has been found convenient to confine the electrolyte 2 to a small region by a boundary wall 13, mounted on the surface layer 5. A bead of silicone sealant has been found convenient for this purpose.

Figure 2:
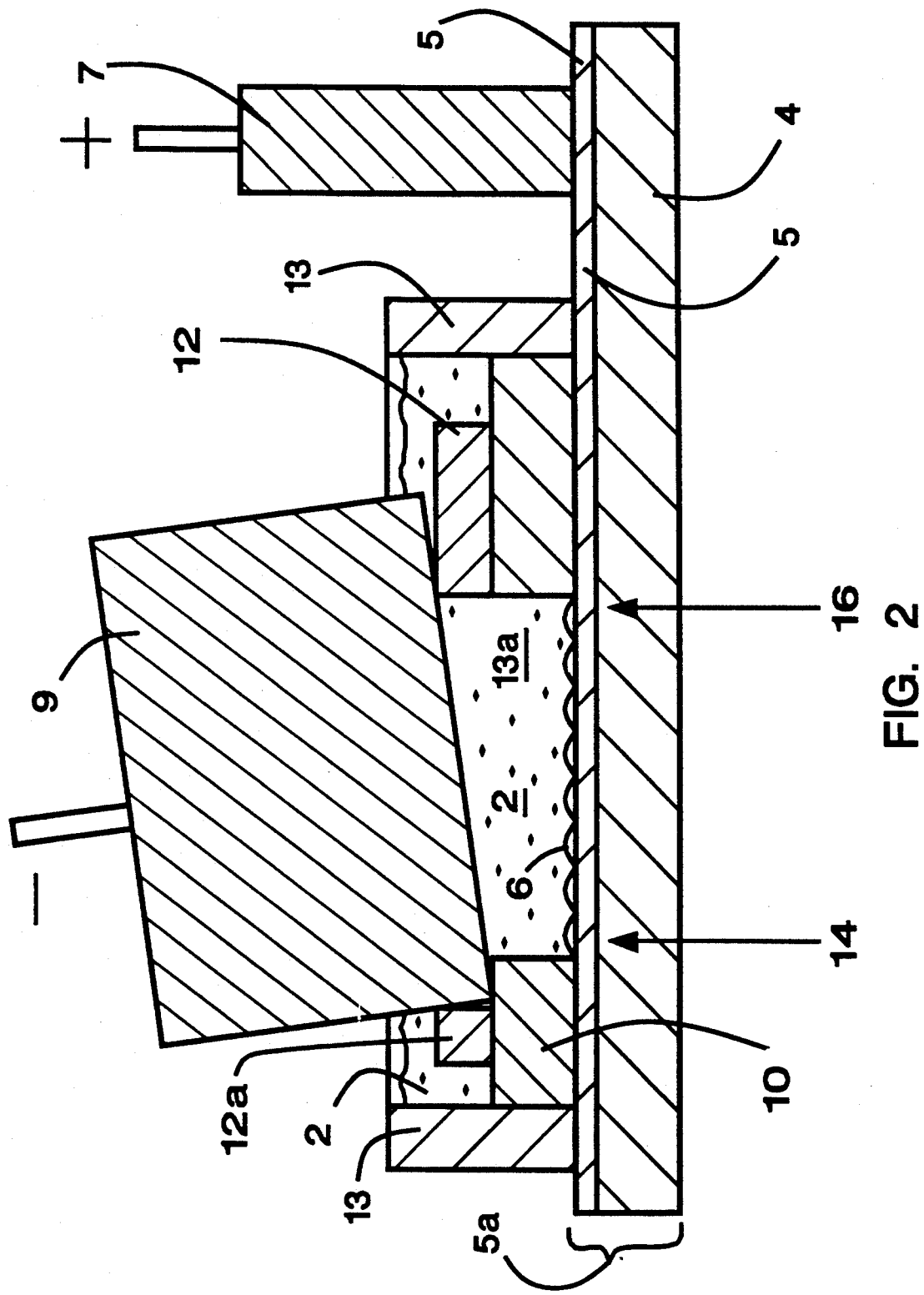
FIG. 2 shows the same inclined electrode arrangement as FIG. 1, wherein electrolyte is confined to a small region by a boundary wall.
Figure 2A:
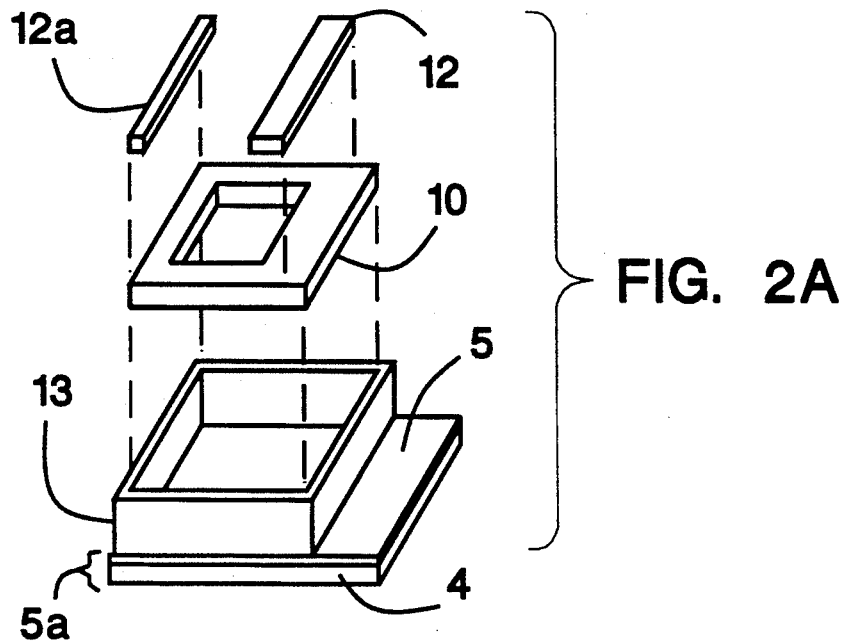

In FIG. 2 and 2a an arrangement is shown wherein the substrate 4 and the surface layer 5 makeup a glass slide 5a carrying such a boundary wall 13. In this case the spacers 10, 12 and stopping bar 12a may be inserted separately into the slide. The level of the electrolyte 2 need only fill the volume 13a above the layer of cells 6 to be electroporated.

By utilizing a very narrow first and second spacer 10, 11, on the order of 300–400 and 800 microns respectively, it has been possible to electroporate cells successfully with applied voltages on the order of 50–130 volts. With 100 volts applied and a gap of 500 microns this is equivalent to a field of 2000 volts/cm over the entire gap. Assuming that the voltage drop across the electrolyte 2 is linear then this same field strength is applied across the cells. This ability to work with lower applied voltages is convenient as it simplifies the controls required for the electrical source.

The narrow gap used between the electrodes 7, 9, combined with boundary wall 13 and slide 5a, also minimizes the quantities of electrolyte containing molecules to be electroporated that are required. This can provide a considerable cost saving where expensive antibodies are being electroporated.

Figure 3:
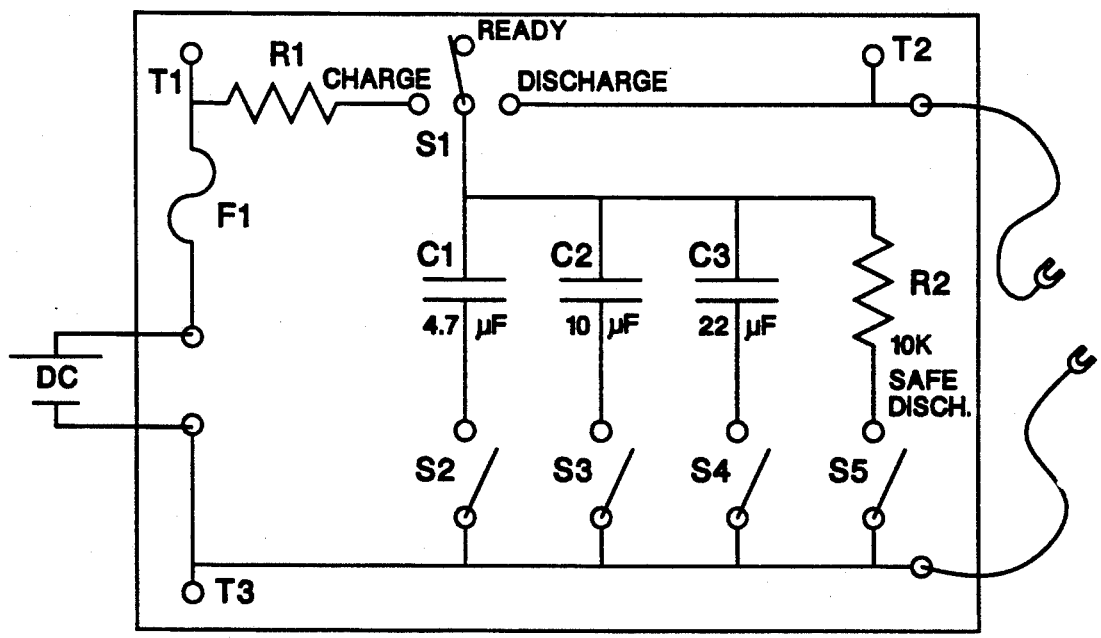
FIG. 3 shows the electrical circuit for supplying electric current to the apparatus.

Cells were electroporated in this set-up utilizing a circuit as shown in FIG. 3 as the electrical source. This figure essentially depicts a capacitor discharge system in which varying capacitors may be selected to supply the charge and current. Generally, the lower electrode 5 was chosen to be positive. The overall momentary system resistance at the point of commencement of the electroporation pulse, was measured as being about 15 ohms. This is only an approximate value based on the initial portion of an exponentially decaying flow of current from the capacitor bank.

Figures 4A, 4B:
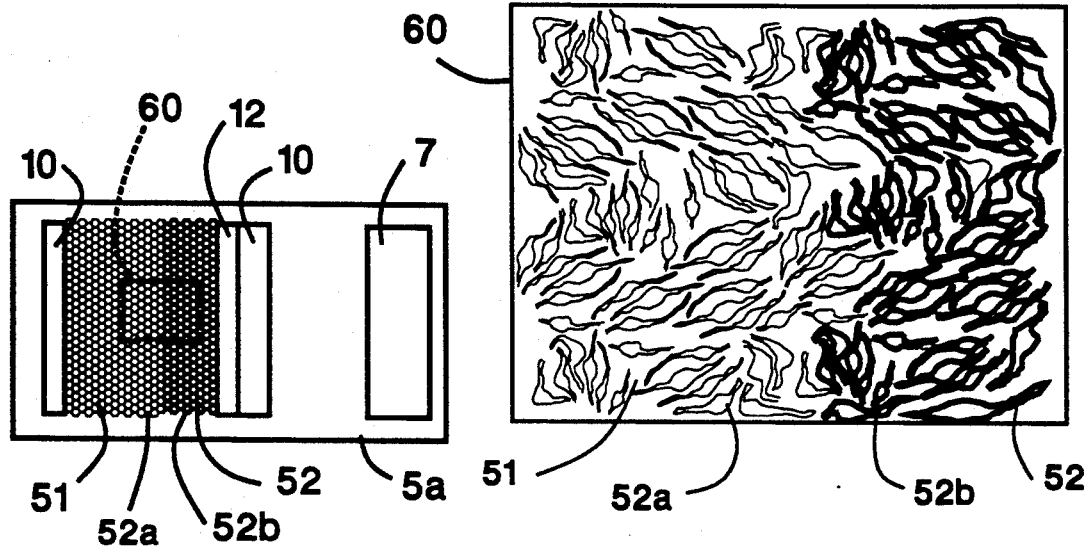
FIG. 4a, b shows the effects of electroporating cells in a non-uniform field.
Figures 5A, 5B:
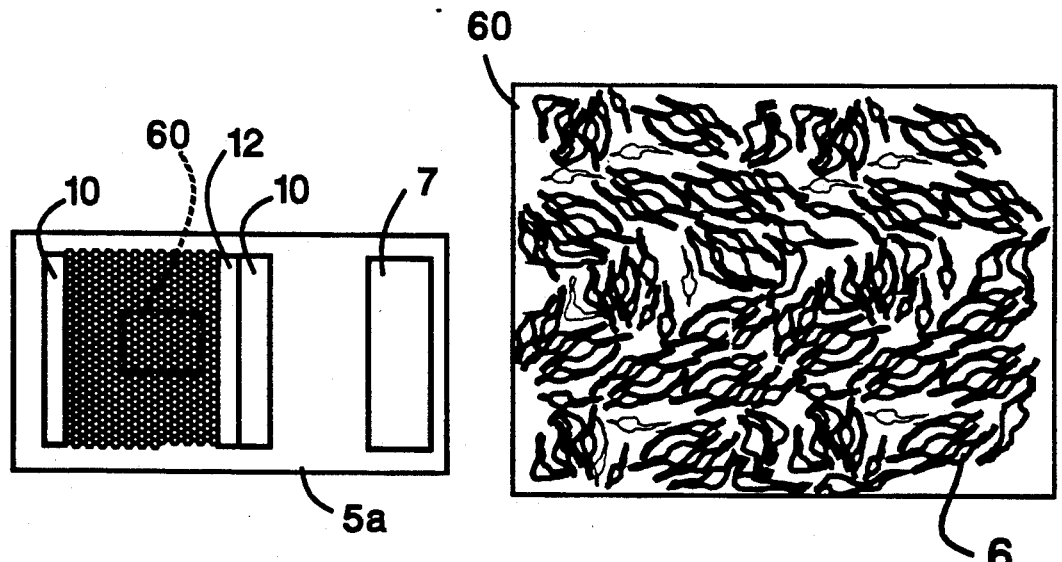
FIG. 5a, b shows the effects of electroporating cells in a uniform field.

It has been found that with the difference in height between the first and second spacers 10, 11 given above when separated by a spacing of 15 millimeters, that relatively uniform successful electroporation of adherent cells can be achieved. The correct angle for the upper electrode 9 to achieve this effect can be determined by trial and error. FIG. 4b shows a photo of the transitional portion 60 of a field of cells on a glass slide 5a that has been electroporated with a non-uniform field. In the region 51 the cells have not been successfully electroporated with molecules carrying a fluorescent marker. In region 52, the spots of fluorescence indicated successful electroporation. By adjusting the shim 12, the degree of electroporation can be made uniform, as in FIG. 5b.

It is believed that the angle of inclination 15 was able to compensate for the proportion of the voltage drop occurring over the surface layer 5 between points 14 and 16, as shown in FIG. 1, and thereby expose the cell population 6 to a uniform field and/or current.

In one set of tests carried-out, the upper electrode 9 was charged negatively and the surface layer 5 positively. The opposed surfaces were 12 by 22 millimeters in lateral dimensions. The assembly was placed inside a 10 cm petri dish and gas or ethanol sterilized. Cells were plated the day before the experiment on the surface layer 5.

Prior to pulse application, the growth medium was removed and the cells washed twice with the electroporation buffer (10 mM Sodium phosphate pH 7.0, 140 mM NaCl, 1 mM Kcl). The same buffer, supplemented with the molecules to be introduced, was subsequently added to the cells. The aluminum negative electrode was set in place and the whole assembly cooled to 4 degrees Centigrade.

A single pulse ranging from 50 to 150 V was delivered from a 32 microfarrad capacitor and the cells incubated at 40 degrees C. for five more minutes. The top electrode was then removed and the cells observed under phase contrast microscopy. For initial permeation studies, trypan blue was added to the cells immediately after the pulse. Cell viability was assessed by the addition of trypan blue 2 hours after electroporation.

For the introduction of antibodies, the cells were electropermeated as above in the presence of 2 mg/ml chicken IgG (Sigma). After the pulse and a 10 min. incubation at 37 degrees C., the unincorporated IgG was removed and the cells washed three times with a solution of 245 mM sucrose, 1 mM Sodium phosphate buffer pH 7.0, 0.1 mM KCl and 14 mM NaCl. Longer incubation times with the IgG resulted in a considerable amount of pinocytosis being observed. The cells were fixed with formalin directly on the electroporation glass slides and the presence of IgG in the cell was assessed by immunostaining using FITC-conjugated anti-chicken IgG.

For stable expression of introduced DNA, F111 cells were electropermeated in the presence of 50 micrograms per ml of pY3 DNA using pulses of increasing field strength. After the shock and a 10 minute incubation at 37 degrees C., the DNA solution was removed and the cells were placed in the incubator in complete medium containing 5% calf serum. Five hours later, the cells were trypsinized and passaged 1:10 into ordinary petri dishes. Selection for hygromycin resistance started three days after electroporation and the number of resistant colonies was scored three weeks later.

Initial tests with the upper negative electrode parallel to the glass surface and two positive contact bars on either side of the lower electrode indicated that cell permeation was much stronger in the regions adjacent to the two positive electrode contacts than in the center of the area exposed to the pulse. The uniformity of permeation was much improved by using a single positive electrode and shimming one end of the negative electrode at an angle.

Chicken IgG and FITC-conjugated anti-chicken IgG (made in rabbits) were purchased from Sigma. [H]-Thymidine was from New England Nuclear and tissue culture media and sera from Flow. The pY3 plasmid was purchased from the American Type Culture Collection, Rockville, Md. The cell line used was Flll a Fisher Rat fibroblast line. All cells were grown in plastic petri dishes in Dulbecco's modification of Eagle's medium (DMEM) supplemented with 5% calf serum in a humidified CO incubator. Selection for Hygromycin resistance was performed as described above.

The optimal voltage for successful electroporation depended upon the metabolic state of the cells. Flll cells plated 3-5 days earlier and allowed to reach confluency required slightly higher voltages than cells plated 20 hours previously. When different cell lines were tested, significant differences in the voltages required for optimal permeation were observed. Mouse N1H3T3 cells or polyoma virus transformed F111 cells (pyF), for instance, needed lower voltages than F111.

In the test setup, the optimal voltage was also found to be dependent upon the degree of spreading of the cells onto the conductive substratum. Densely growing cells or cells in a clump needed higher voltages for optimum permeation than sparse, subconfluent cells. Similarly, cells that had been detached from their growth surface by vigorous pipetting prior to electroporation required higher applied voltages (98V, as opposed to 85 V, see below). It was especially striking that cells in mitosis and hence not well spread onto the conductive surface, remained intact under conditions which permeated most cells in other phases of the cycle. This could be related to the more relaxed nature of the cell membrane during mitosis, or to the larger amounts of current passing through an extended cell.

Figure 6:
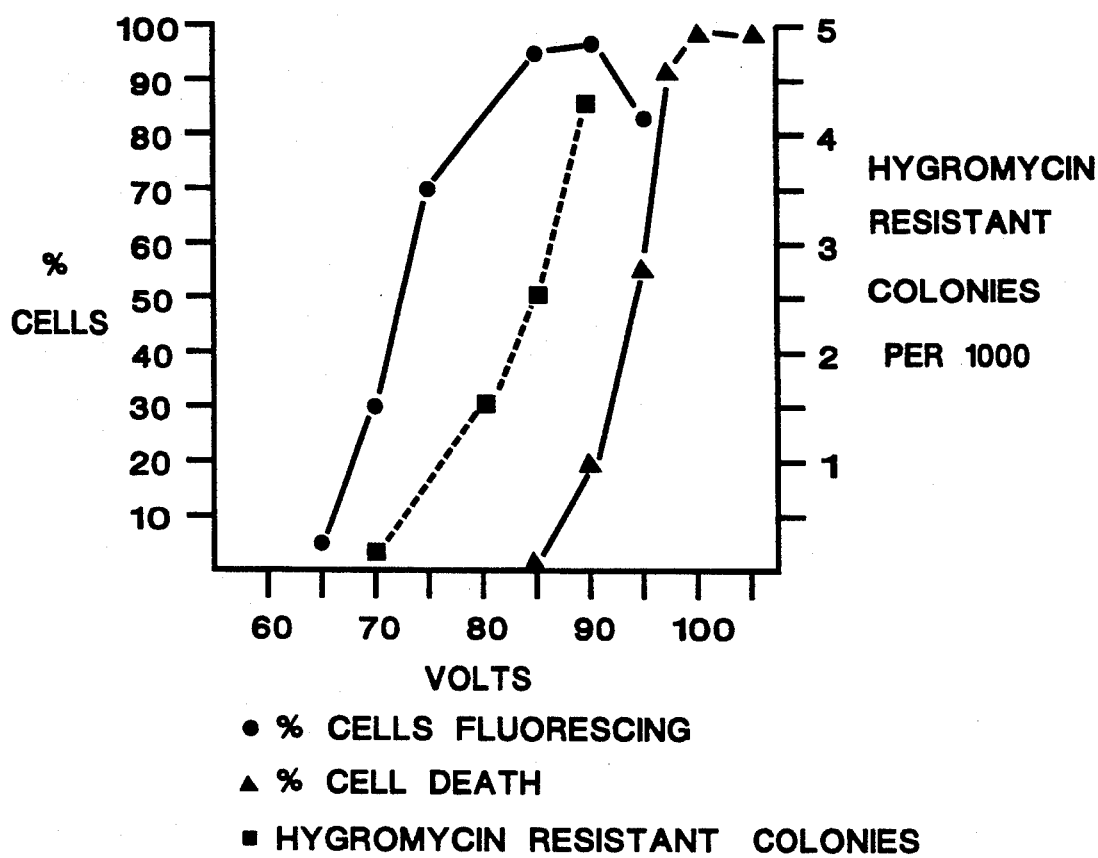
FIG. 6 is a graph showing the effects of increasing the applied voltage on both successful electroporation and on cell death.

The results of a typical experiment are shown in FIG. 6 where electroporation is shown as a function of the applied voltage, and therefore of field strength. Pulses of increasing applied voltage were applied to the cells in the presence of 2 mg/ml IgG or 50 micrograms/ml pY3 DNA. Cell killing was assessed by the addition of trypan blue two hours after the pulse. After the pulse, cells were probed for incorporated antibody, or selected for hygromycin resistance.

This figure shows dramatically the critical range of applied voltages found suitable to effect successful electroporation.

The application of an exponentially-decaying pulse of an initial strength of 85 V resulted in almost 100% of the cells containing the introduced IgG. Pulses lower than 70 V did not result in any antibody introduction, while pulses of 95 V killed most of the cells, sparing cells in mitosis. An assay for the presence of the antibodies at different times after the pulse indicated that these molecules persisted in the cytoplasm for at least 24 hours.

Antibodies microinjected into the cytoplasm of adherent cells invariably do not penetrate the nuclei. Application of relatively low voltages (70 V) resulted in the introduction of the antibodies almost exclusively into the cytoplasm of approximately 30% of the cells. However, an 85 V pulse resulted in the introduction of the antibodies into both the cytoplasm and the nucleus.

Therefore, careful control of the field strength might permit antibody incorporation preferentially into the cytoplasm.

Effect of permeation upon the cell division cycle

The potential of this technique for the study of the cell cycle was evaluated by assessing the length of the prereplicative development of electroporated normal cells stimulated to grow by serum addition, as compared to control, nonelectroporated cells.

Flll cells were seeded into electroporation chambers. When 50% confluent, these cells were arrested in the Go/Gl phase by a severe serum deprivation for 40 hrs. One hour after the addition of 10% serum, an electrical discharge of varying strength was applied to the presence of 2 mg/Ml 1 gG as above, and the entry of the cells into the S phase was monitored by a 2-hr [H]-thymidine pulse at different times starting at 8 hrs., followed by autoradiography As shown in Table 1, there was no significant delay in the entry of the electroporated cells in the S phase under conditions of efficient antibody introduction. Moreover, no increase in the overall cell cycle length was observed after electroporation indicating that, under carefully controlled conditions, IgG introduction has no measurable effect upon the cell cycle, making this technique a potentially valuable tool for the study of cell division.

TABLE 1

| Field Strength (Volts) | % cells in S phase after | |
| --- | --- | --- |
| | 12 hours | 14 hours |
| 0 | 92 | 90 |
| 75 | 89 | 92 |
| 80 | 95 | 96 |
| 85 | 92 | 88 |

Stable Expression of Electroporated DNA

The potential application of this technique in the stable expression of introduced genetic material was examined by measuring the efficiency of expression of the gene conferring resistance to hygromycin through the introduction of plasmid pY3, containing this gene under control of the Murine Leukemia Virus promotor. As shown in FIG. 6, higher voltages were necessary for the best yield of stable transfectants to be obtained, than for the introduction of antibodies; however, a substantial number of cells were killed under these conditions, as evidenced by trypan blue staining. Nevertheless, approximately five cells out of 1000 electroporated revealed a stable expression of the hygromycin resistance gene under the optimal conditions. This is substantially higher than the efficiency of transfection of this line by the Calcium phosphate technique, as well as the published values of stable expression after liposome fusion. Besides, this technique, by permitting the synchronization of the cells and electroporation without the disturbance to cell division caused by the detachment, offers the potential of pulse application at distinct stages of the cell division cycle, which could improve these figures even further.

The foregoing tests were carried-out with the electrode polarity as indicated. These polarities may be reversed to expose the cells 6 on the side facing the opposed electrode to a reverse electric field. This effect is not possible with cells in suspension.

Figure 7:
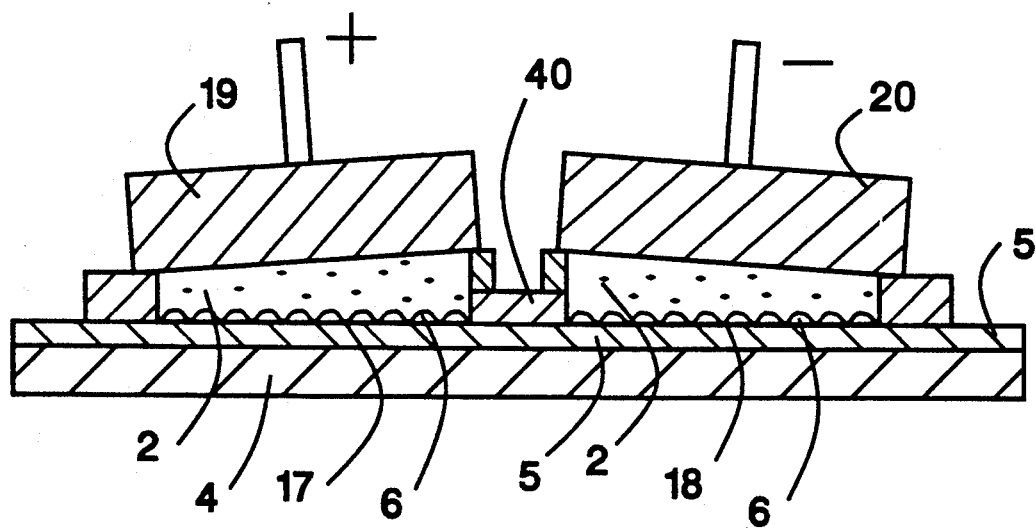
FIG. 7 shows a dual upper electrode arrangement by which a slide carrying adhered cells may be exposed simultaneously to the same electric current, but with opposite field polarity on each of the two portions of the slide.

A convenient proposed configuration that will allow tests to be conducted that compare polarity effects is shown in FIG. 7. In FIG. 7 the surface layer 5 is not attached directly to a voltage/current source. Instead an impermeable insulative barrier 40 isolates the electrolyte 2 above a first region 17 from the electrolyte 2 above a second region 18. Mirror symmetric positive and negative electrodes 19, 20 are mounted above each region 17, 18. Optionally, these may be inclined to provide electric fields of constant strength over the surface layer 5.

By applying voltage and supplying current through the upper electrodes 19, 20 both of which are suspended in the electrolyte 2, the effects of reverse polarity electroporation on cells 6 may be compared on a side-by-side basis.

Figure 8:
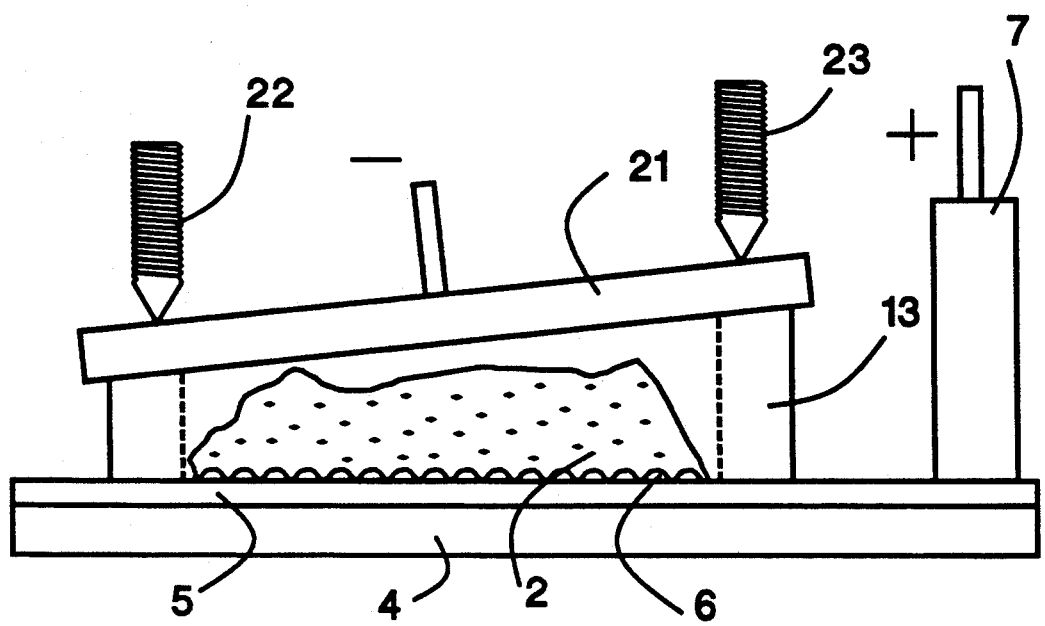
FIG. 8 shows an electroporation slide with a resilient, crushable boundary wall that is supporting an upper electrode at an adjustable angle.

A further alternate configuration is shown in FIG. 8. Here the boundary wall 13 is a precisely formed structure, of resilient material, and the upper electrode 21 overlies this wall. Adjustable screws 22, 23 (held by structures not shown) allow this electrode 21 to be inclined in a controlled manner while further reducing the volume of the electrolyte being utilized.

Figure 9A:
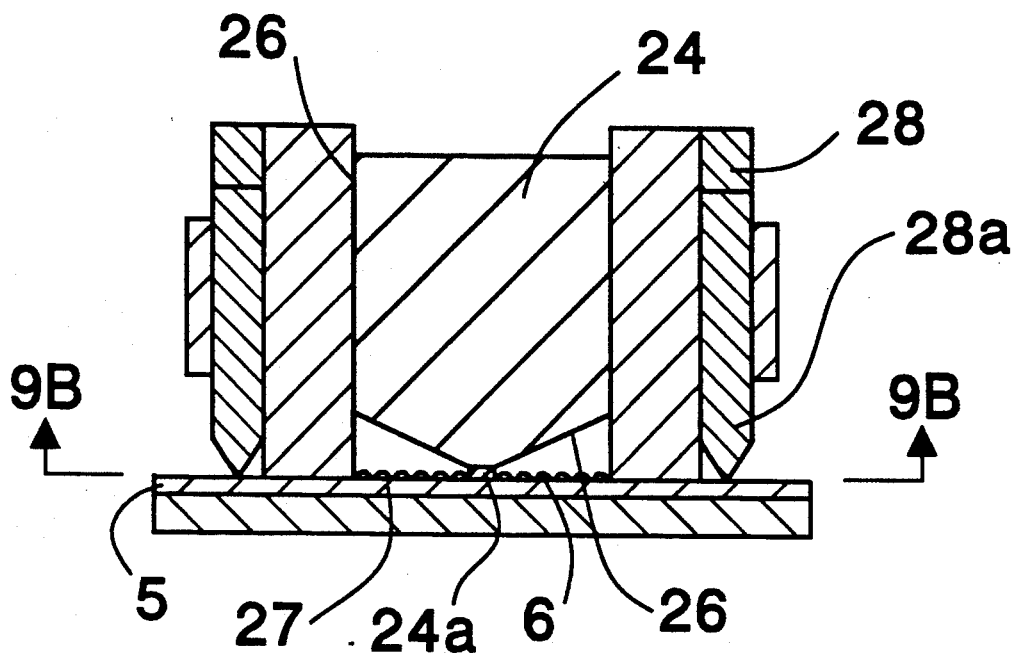
FIG. 9a, b show an electroporation arrangement in which a circular partially-conductive cell supporting surface is contacted circumferentially and exposed to a field from a conically shaped upper electrode.
Figure 9B:
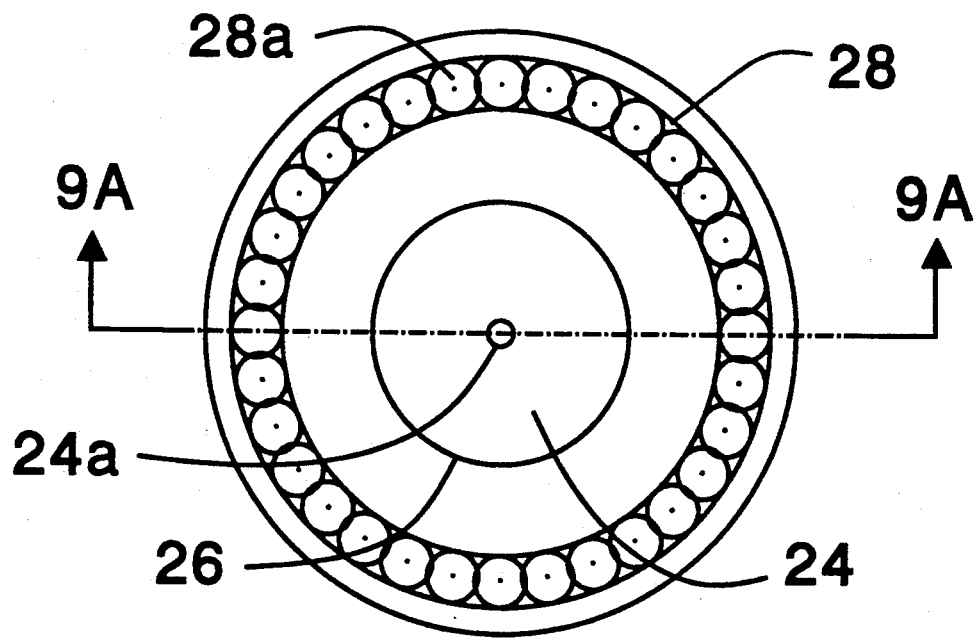

A uniform field can also be created with other geometric configurations. FIG. 9a, b shows the use of a central upper electrode 24 with a conical end surface 25 and cylindrical outer boundary 26. An insulative spacer 24a supports this electrode 24. Current from the other electrode surface 27 is supplied from an outer circular ring 28 that contacts the surface layer 5 through contact pins 28a. The conical angle and spacing between the conical end surface 25, combined with the voltage drop over the surface layer 5 are chosen so as to provide a uniform field over the cells 6 on the surface layer 5.

Figure 10:
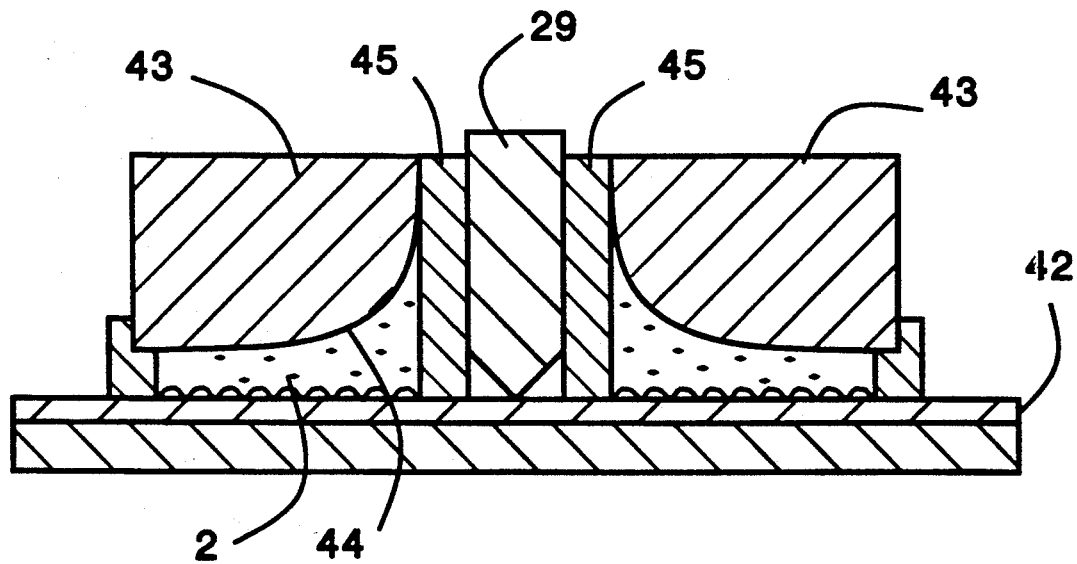
FIG. 10 shows an electroporation arrangement in which a circular partially-conductive cell-supporting surface is contacted centrally and exposed to a field from a radially symmetrical, curved upper electrode.

FIG. 10 shows another geometric configuration in which the lower electrode 42 is contacted by a rod 29, centrally and the upper electrode 43 is provided with a radially symmetrical surface 44 having the radial cross-section of a curve, probably second order, which creates the requisite constant field condition at the surface of the lower electrode. A cylindrical insulating sleeve 45 isolates the rod 29 from the electrolyte 2.

Figure 11:
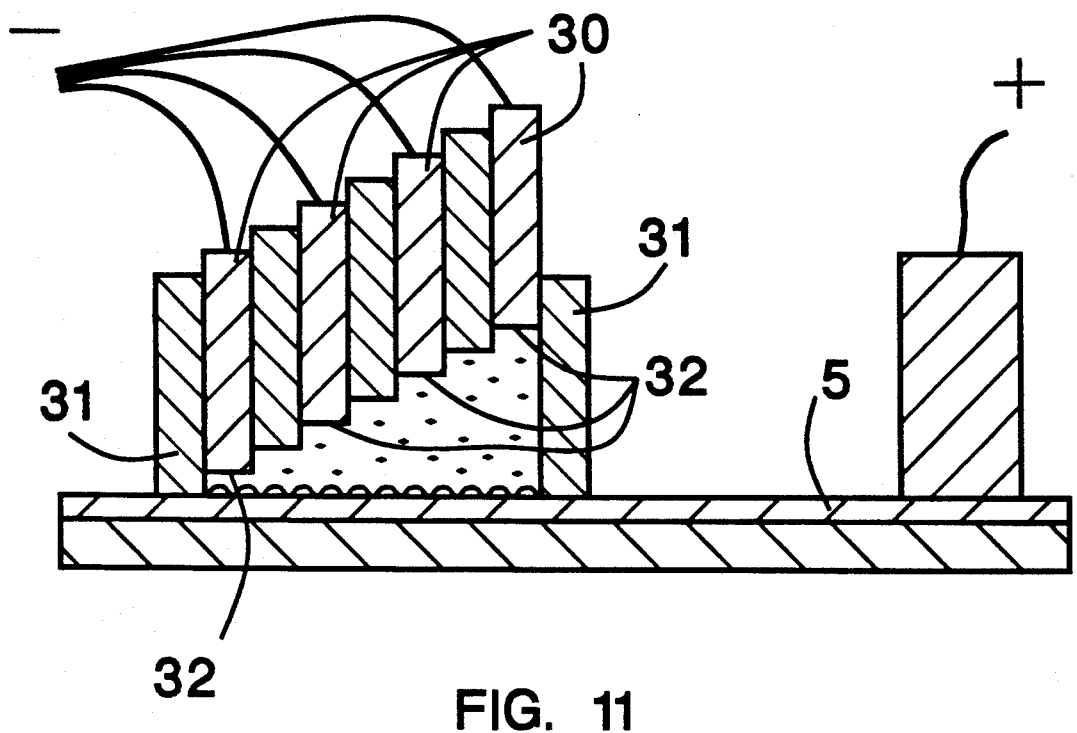
FIG. 11 shows an electroporation arrangement wherein the upper electrode is segmented into electrode elements that are staggered obliquely to create a constant or graded electric field on the layer of cells below.

FIG. 11 shows an arrangement equivalent to an inclined electrode in which multiple staggered conductive plates 30 are separated by insulators 31. The ends 32 of such plates will approximate the effect of an inclined planar electrode. Again, the spacing above the surface layer 5 may be arranged to create a constant field condition.

Figure 12:
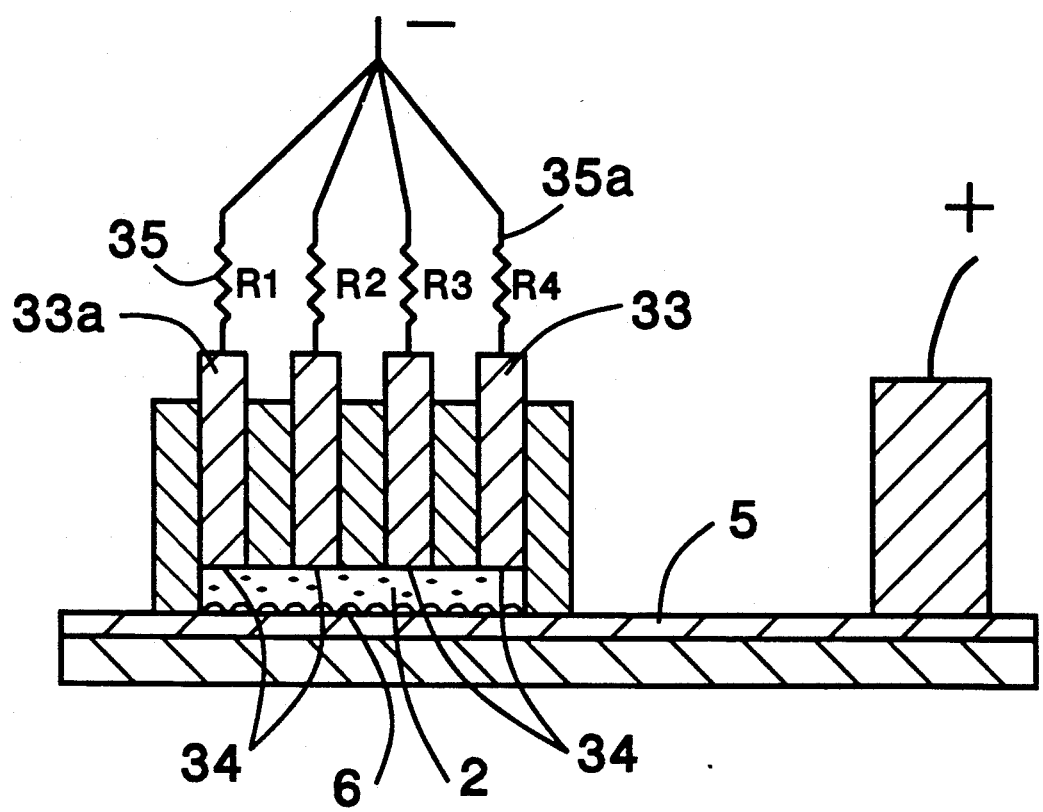
FIG. 12 shows an electroporation arrangement wherein the upper electrode is segmented into electrode elements that present ends that are parallel to the cell surface, and are fed current through individual resistors that control the electrical field developed over the cell surface.

FIG. 12 shows a non-geometric means for controlling field strength. The separated upper electrode elements 33 of the upper composite electrode 33a have their ends 34 equidistant from the surface layer 5, but the requisite constant field strength over the surface layer 5 is obtained by supplying voltage and current to each electrode 33 through a differing resistor 35,35a etc. The voltage drops across each resistor may be chosen to create a constant field over the surface layer 5. This, in effect, provides an upper source of electric potentials which may be adjusted to be complementary to the potentials over the surface of the lower electrode, and thereby achieve constant local field values over the surface of the lower electrode.

Such a configuration may also be used to approximate the correct inclination of a solid-block electrode. This may be done by utilizing resistors of equal value and inclining the composite electrode until equal current flows are measured in each electrode element 33. The angle of inclination thus determined will approximate that for a solid block electrode.

The foregoing configurations premise use of a surface layer 5 that exhibits a voltage drop. An alternate mode for minimizing the effect of such a drop is to provide voltage and current to this layer 5 at a multiple number of locations distributed over that layer 5.

Figure 13:
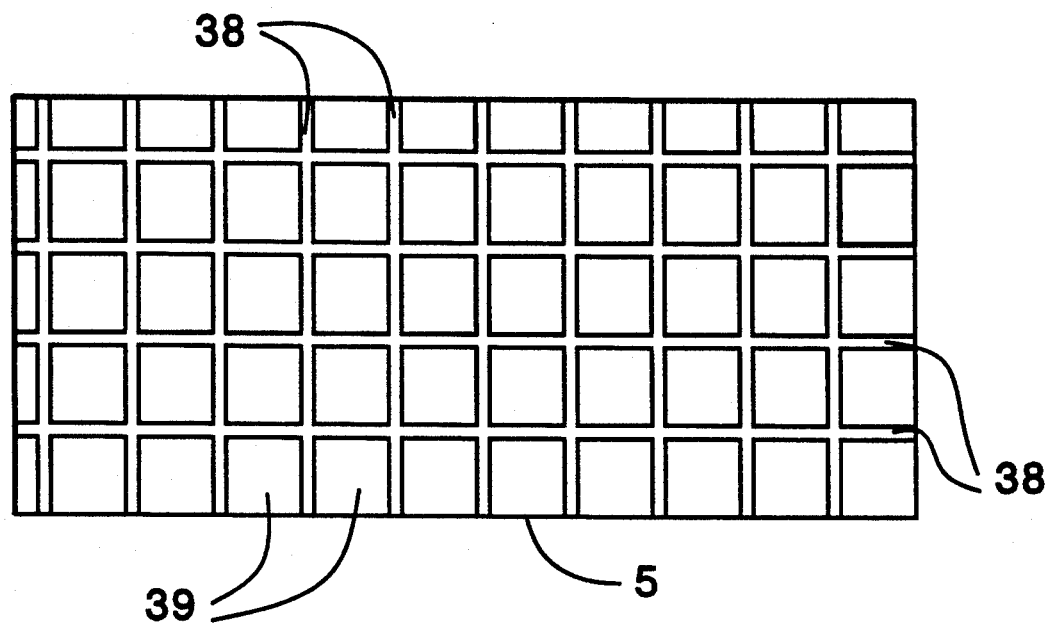
FIG. 13 shows a transparent slide suitable for carrying a partially conductive, transparent surface layer that is supplied current through a grid or matrix of thin, opaque conductive strips that contact the surface layer.

FIG. 13 shows a grid of ribbons or lines 38 of conductive material, such as aluminum, formed beneath or above the partially conductive, transparent surface layer 5 of a transparent slide. Such lines 38 may be vacuum deposited utilizing a mask. Between lines 38 small voltage drops will occur. But these drops may be made small enough, by selecting line 38 density, to ensure that all areas over the surface layer 5 are exposed to local electrical field strengths appropriate to successful electroporation. Even if the lines 38 are opaque, cells may be viewed in the regions 39 between lines 38.

Figure 14:
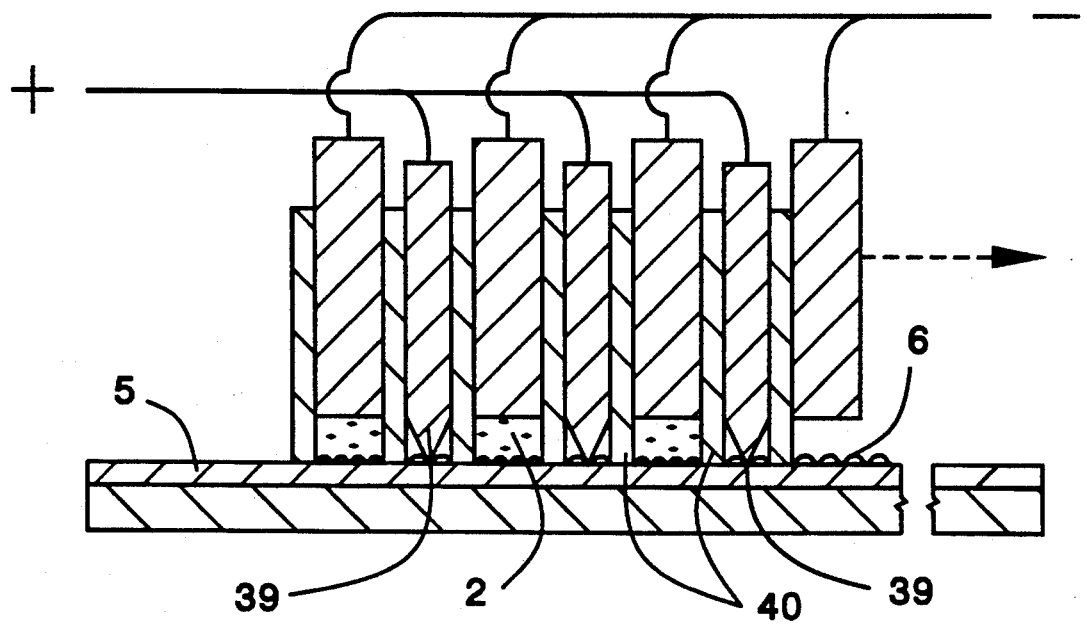
FIG. 14 shows an electroporation arrangement wherein the upper electrode is segmented into electrode elements that present ends that are parallel to the cell surface, and the partially electrically conductive surface layer on which cells are growing is contacted by contacting bars which are interspersed with the upper electrode elements and which descend from above to provide electrical contact with the surface layer.

FIG. 14 shows another configuration of this class wherein the contacts supplying voltage and current to the surface layer 5 are provided by alternating lower electrode contactors 39 descending through the electrolyte 2 and penetrating through the cell layers 6 to contact the conductive surface layer 5 with a conductive, preferably knife-edge, end. To limit current flow to substantially the surface layer 5, each descending electrode contactor 39 is provided with an interspersed insulative layer 40 on both sides separating it from the electrolyte 2.

Throughout, reference has been so far to the use of the described configurations to overcome a voltage drop occurring in a thin film, and to create a constant field over a population of cells attached to such a surface. The use of a thin film, presumed to be only partially conductive, was chosen by reason that a thin film may be sufficiently transparent to enable viewing of the cells in a microscope. If a non-resistive substrate were utilized for the cells, no voltage drop would occur. Then efforts to angle planar electrodes, or space electrode surfaces generally, would not be necessary in order to create uniform local electric fields.

However, all of the foregoing configurations are useful, even with a substrate for the cell population that exhibits no, or a negligible, voltage drop. Such configurations may also be used to create, over a cell population attached to a fully conductive surface, a local electrical field which varies over that surface in a continuous geometrically regular manner.

Thus two fully conductive, opposed, planar electrodes in inclined orientation will create a field which varies linearly, in progressing in one direction over the surface of one of the electrodes. The variation need not be linear, if other surface shapes, or distributions of resistance are employed. But the field variation may be controlled and caused to vary in a continuous manner over the cell population.

An advantage of such an arrangement is that cells of the same population may be electroporated under closely similar fields. This has the benefit of allowing the effects of variations in field strength to be observed on a single slide. FIG. 4 provides an example of such a result.

Furthermore, when it has been determined that certain cells are desired that have been electroporated at a precise or narrow range of field strengths, a cell population treated with a uniformly and continuously varying field may be separated physically. This will allow segregation of the cells exposed exclusively to the preferred field strength.

In FIG. 4b within the region of successful electroporation 52, it is possible to segregate cells from differing areas 52a, 52b, for examination and treatment based on the fact that they were electroporated under fields of differing strength.

Conclusion

A series of devices and methods have been described suitable for electroporating cells adhering to a surface under conditions of constant local electrical fields strength; or under local electrical fields which vary in a continuous, geometrically regular manner over the surface.

While a series of specific structures embodying the invention have been shown and described herein, it will be clear to those skilled in the art that various modifications and rearrangements of parts may be made without departing from the spirit and scope of the inventive concept. Accordingly, the invention is not limited to the particular forms of embodiments herein shown and described.

The foregoing has set forth a series of exemplary embodiments of the invention. The invention in its most general and more particular aspects is further described and defined in the claims which now follow.

I claim:

1. An electroporation apparatus for electroporating living cells with molecules comprising:
   (a) first and second electrodes, respectively having, first and second mutually opposed electrode surfaces, said first and second mutually opposed electrode surfaces being positioned to create an electric field there-between when connected to a source of electrical potential, said first electrode being only partially conductive and exhibiting a voltage drop across its said first electrode surface upon the passage of current therethrough;
   (b) an electrolyte positioned between said first and second said electrolyte containing molecules to be deposited within living cells by electroporation and being in contact with said first and second electrode surfaces;
   (c) living cells attached to said first electrode surface and being in contact with said electrolyte, and
   (d) containment means positioned to contain the electrolyte and living cells between said first and second electrodes, wherein by reason of the spacing between opposed portions of said first and second mutually opposed electrode surfaces, said second electrode, in combination with said first electrode, provides a local electrical field over said first electrode surface which is of substantially equal strength over said first electrode surface.

2. An apparatus as in claim 1 wherein said first and second mutually opposed electrode surfaces are planar.

3. An apparatus as in claim 2, wherein said second electrode surface is angled with respect to said first electrode surface to create along said first electrode surface said local electrical field of substantially equal strength.

4. An apparatus as in claim 1, 2 or 3 wherein;
   (a) said first electrode comprises a non-conductive substrate;
   (b) said first electrode surface comprises a partially conductive layer bonded to said non-conductive substrate, and
   (c) said non-conductive substrate and partially conductive layer are sufficiently transparent or translucent to allow viewing of the living cells on said first electrode surface under a microscope by transmitted light.

5. An apparatus as in claim 1, 2 or 3 wherein said first electrode comprises a, partially conductive planar layer deposited on a non-conducting substrate and wherein said containment means comprises an encircling, elevated boundary wall formed on said layer, partially conductive planar delimiting an area on the surface of said partially conductive planar layer for containment of said electrolyte.

6. An apparatus as in claim 5 wherein said non-conducting substrate and partially conductive planar layer are sufficiently transparent or translucent to allow viewing of the living cells on said first electrode surface under a microscope by transmitted light.

7. An electroporation apparatus for electroporating living cells with molecules comprising:
(a) first and second electrodes, mutually having, first and second mutually opposed electrode surfaces, said first and second mutually opposed electrode surfaces being positioned to create an electric field there-between when connected to a source of electrical potential, said first electrode being only partially conductive and exhibiting a voltage drop across its said first electrode surface upon the passage of current therethrough;
(b) an electrolyte positioned between said first and second electrodes, said electrolyte containing molecules to be deposited within living cells by electroporation and being in contact with said first and second mutually opposed electrode surfaces;
(c) cells attached to said first electrode surface and being in contact with said electrolyte, and
(d) containment means positioned to contain the electrolyte and living cells between the said first and second electrodes, wherein said second electrode surface is angled with respect to said first electrode surface whereby said second electrode, in combination with said first electrode, provides a local electrical field over said first electrode surface which is of a strength which varies in a continuous, increasing, regular manner when proceeding in a given direction along said first electrode surface.

8. An apparatus as in claim 7 wherein said first and second electrode surfaces are planar.

9. An apparatus as in claim 7 or 8 wherein;
(a) said first electrode comprises a non-conductive substrate;
(b) said first electrode surface comprises partially conductive layer bonded to said non-conductive substrate, and
(c) said non-conductive substrate and partially conductive layer are sufficiently transparent or translucent to allow viewing of the living cells on said first electrode surface under a microscope by transmitted light.

10. An apparatus as in claim 7 or 8 wherein said first electrode comprises a partially conductive planar layer deposited on a non-conducting substrate and wherein said containment means comprises an encircling, elevated boundary wall formed on said partially conductive planar layer, delimiting an area on the surface of said partially conductive planar layer for containment of said electrolyte.

11. An apparatus as in claim 10 wherein said non-conducting substrate and partially conductive planar layer are sufficiently transparent or translucent to allow viewing of the living cells on said first electrode surface under a microscope by transmitted light.

12. An electroporation apparatus for electroporating living cells with molecules comprising:
(a) first and second electrodes, respectively having, first and second mutually opposed electrode surfaces, said first and second mutually opposed electrode surfaces being positioned to create an electric field there-between when connected to a source of electrical potential, said first electrode being only partially conductive and exhibiting a voltage drop across its said first electrode surface upon the passage of current therethrough;
(b) an electrolyte positioned between said first and second electrodes, said electrolyte containing molecules to be deposited within living cells by electroporation and being in contact with said first and second mutually opposed electrode surfaces;
(c) living cells attached to said first electrode surface and being in contact with said electrolyte;
(d) containment means positioned to contain the electrolyte and living cells between said first and second electrodes; and
(e) voltage control means for establishing differing voltage potentials at specific locations over said second electrode surface, said voltage control means thereby determining the local strength of said electric field over said first electrode surface according to the pattern of the voltage potential developed at such locations.

13. An electroporation apparatus as in claim 12 wherein said second electrode, in combination with said first electrode, provides a local electrical field over said first electrode surface which is of a substantially equal strength over said first electrode surface.

14. An electroporation apparatus as in claim 12 wherein said second electrode, in combination with said first electrode, provides a local electrical field over said first electrode surface which is of a strength which varies in a continuous, increasing regular manner when proceeding in a given direction along said first electrode surface.

15. An apparatus as in claims 12, 13, or 14 wherein:
(a) said first electrode comprises a non-conductive substrate;
(b) said first electrode surface is provided with a partially conductive layer bonded to said non-conductive substrate; and
(c) said non-conductive substrate and layer partially conductive layer are sufficiently transparent or translucent to allow viewing of the living cells on said first electrode surface under a microscope by transmitted light.

16. An apparatus as in claim 12, 13 or 14 wherein said first electrode comprises a partially conductive planar layer deposited on a non-conducting substrate and wherein said containment means comprises an encircling, elevated boundary wall formed on said partially conductive planar layer, delimiting an area on the surface of said partially conductive planar layer for containment of said electrolyte.

17. An apparatus as in claim 16 wherein said non-conducting substrate and partially conductive planar layer are sufficient transparent or translucent to allow viewing of the living cells on said exposed surface under a microscope by transmitted light.

18. An electroporation apparatus as in claims 12, 13 or 14 wherein said second electrode comprises segmented portions, each of said segmented portions being separated from adjacent segmented portions by insulation means, and each of said segmented portions being connected to a source of voltage potential through individual resistance means to thereby establish said voltage potential at specific locations over said second electrode surface.

19. An electroporation apparatus for electroporation apparatus living cells with molecules comprising:
    (a) first and second electrodes, having respectively having, first and second mutually opposed electrode surfaces, said first and second mutually opposed electrode surfaces being positioned to create an electric field there-between when connected to a source of electrical potential, said first electrode being only partially conductive and exhibiting a voltage drop across its first electrode surface upon the passage of current therethrough;
    (b) an electrolyte positioned between said first and second electrodes, said electrolyte containing molecules to be deposited within living cells by electroporation and being in contact with said first and second mutually opposed electrode surfaces;
    (c) living cells attached to said first electrode surface and being in contact with said electrolyte, and
    (d) containment means positioned to contain the electrolyte and living cells between said first and second electrodes, wherein said first electrode is provided with a plurality of conductive strips that are distributed over a substantial portion of said first electrode surface whereby said plurality of conductive strips are able to provide current to said first electrode surface with a reduced degree of voltage drop across said first electrode surface over that which would occur in the absence of such plurality of conductive strips.

20. An electroporation apparatus in claim 19 wherein said second electrode, in combination with said first electrode, provides a local electrical field over the electrode surface of said first electrode which is of a substantially equal strength over said first electrode surface.

21. An electroporation apparatus as in claim 19 wherein said second electrode, in combination with said first electrode, provides a local electrical field over the electrode surface of said first electrode which is of a strength which varies in a continuously, increasing regular manner when proceeding in a given direction along the electrode surface of said first electrode.

22. An apparatus as in claim 19, 20 or 21 wherein:
    (a) said first electrode comprises a non-conductive substrate;
    (b) said first electrode surface is provided with a partially conductive layer bonded to said non-conductive substrate; and
    (c) said non-conductive substrate and partially conductive layer are sufficiently transparent or translucent to allow viewing of the living cells on said first electrode surface under a microscope by transmitted light.

23. An apparatus as in claims 19, 20 or 21 wherein said first electrode comprises a partially conductive planar layer deposited on a non-conducting substrate and wherein said containment means comprises an encircling, elevated boundary wall formed on said partially conductive planar layer, delimiting an area on the surface of said partially conductive planar layer for containment of said electrolyte.

24. An apparatus as in claim 23 wherein said non-conducting substrate and partially conductive layer are sufficiently transparent or translucent to allow viewing of the living cells on said first electrode surface under a microscope by transmitted light.

* * * * *